US011007306B2

(12) United States Patent
Yang et al.

(10) Patent No.: US 11,007,306 B2
(45) Date of Patent: May 18, 2021

(54) MEDICAL DEVICE LUBRICANT SYSTEM AND METHODS OF USE

(71) Applicant: JB MEDICAL, INC., Suzhou (CN)

(72) Inventors: Jibin Yang, Sparta, NJ (US); Yaguo Jiang, Wujiang (CN)

(73) Assignee: JB MEDICAL, INC., Suzhou (CN)

( * ) Notice: Subject to any disclaimer, the term of this patent is extended or adjusted under 35 U.S.C. 154(b) by 528 days.

(21) Appl. No.: 15/547,493

(22) PCT Filed: Jan. 11, 2016

(86) PCT No.: PCT/CN2016/070545
§ 371 (c)(1),
(2) Date: Jul. 29, 2017

(87) PCT Pub. No.: WO2016/119586
PCT Pub. Date: Aug. 4, 2016

(65) Prior Publication Data
US 2018/0021484 A1 Jan. 25, 2018

(30) Foreign Application Priority Data

Jan. 30, 2015 (CN) .......................... 201510051623.6

(51) Int. Cl.
A61L 31/10 (2006.01)
C10M 107/50 (2006.01)
C08K 5/544 (2006.01)
C08G 77/16 (2006.01)
C08L 83/04 (2006.01)
C10N 10/08 (2006.01)
C10N 20/02 (2006.01)
C10N 20/04 (2006.01)
C10N 40/00 (2006.01)
C10M 173/00 (2006.01)

(52) U.S. Cl.
CPC .............. A61L 31/10 (2013.01); C08K 5/544 (2013.01); C10M 107/50 (2013.01); C08G 77/16 (2013.01); C08L 83/04 (2013.01); C10M 173/00 (2013.01); C10M 2201/102 (2013.01); C10M 2207/021 (2013.01); C10M 2229/02 (2013.01); C10N 2010/08 (2013.01); C10N 2020/02 (2013.01); C10N 2020/04 (2013.01); C10N 2040/50 (2020.05)

(58) Field of Classification Search
CPC ......... A61L 31/10; C08L 83/04; C08K 5/544; C10M 107/50; C10N 2040/50
See application file for complete search history.

(56) References Cited

U.S. PATENT DOCUMENTS

| 4,938,827 | A | * | 7/1990 | Leach | ........................ | C08J 5/12 |
| | | | | | | 156/272.6 |
| 5,108,782 | A | * | 4/1992 | Reed | ........................ | C09J 7/401 |
| | | | | | | 427/515 |
| 5,338,312 | A | | 8/1994 | Montgomery | | |
| 8,785,507 | B2 | * | 7/2014 | Bloomfield | ............ | C08G 77/56 |
| | | | | | | 521/52 |
| 9,434,857 | B2 | * | 9/2016 | Ou | ........................ | A61L 29/085 |
| 2001/0021832 | A1 | | 9/2001 | Numao et al. | | |
| 2004/0209784 | A1 | * | 10/2004 | Hardman | ............... | A61L 29/085 |
| | | | | | | 508/204 |
| 2007/0060952 | A1 | * | 3/2007 | Roby | ................... | A61B 17/115 |
| | | | | | | 606/219 |
| 2014/0277120 | A1 | * | 9/2014 | Cichocki | .......... | A61B 17/06066 |
| | | | | | | 606/222 |

FOREIGN PATENT DOCUMENTS

| CN | 104105765 A | 10/2014 |
| EP | 0612811 A2 | 8/1994 |
| JP | 2001-190654 A | 7/2001 |
| JP | 2010-100667 A | 5/2010 |

OTHER PUBLICATIONS

Chinese Notification of the Granting of an Invention Patent, dated Jul. 4, 2019, for Chinese Application No. 201510051623.6, with English translation.
Chinese Office Action dated Oct. 24, 2016, for Chinese Application No. 201510051623.6, with English translation.
Chinese Office Action, dated Jan. 12, 2018, for Chinese Application No. 201510051623.6, with English translation.
Chinese Office Action, dated Jun. 27, 2018, for Chinese Application No. 201510051623.6, with English translation.
Chinese Office Action, dated Jun. 7, 2017, for Chinese Application No. 201510051623.6, with English translation.
Chinese Office Action, dated Nov. 30, 2018, for Chinese Application No. 201510051623.6, with English translation.
Chinese Office Action, dated Sep. 21, 2017, for Chinese Application No. 201510051623.6, with English translation.
Extended European Search Report, dated Jun. 25, 2018, for European Application No. 16742648.5.
Xiang et al., "Basics of Adhesive and Formula Design," Chemical Industrial Press, Beijing, Dec. 2001, ISBN 7-5025-3599, pp. 97-99 (7 pages total), with a partial English translation.

* cited by examiner

Primary Examiner — Dah-Wei D. Yuan
Assistant Examiner — Andrew J Bowman
(74) Attorney, Agent, or Firm — Birch, Stewart, Kolasch & Birch, LLP

(57) ABSTRACT

The present invention disclosed a lubricant system and methods of use. Said lubricant system comprises siloxane polymers with viscosity greater than 100 centistokes and cross-linking agents that can promote siloxane polymers curing rapidly in ambient conditions. The lubricant system comprises further hydroxy siloxane polymers, siloxane coupling agent, catalyst and volatile carrier solvents. The surfaces of medical devices are coated at least once, a solid lubrication film can be quickly formed, and the film has a very excellent lubricating performance and wide applications. The methods of use are simple, easy to implement and control, and is particularly suitable for rapid automatic production lines, and thus is of great economic value.

16 Claims, No Drawings

MEDICAL DEVICE LUBRICANT SYSTEM AND METHODS OF USE

CROSS-REFERENCE TO RELATED APPLICATION

The present application is a National Stage International Patent Application No. PCT/CN2016/070545, filed 11 Jan. 2016, which claims foreign priority benefits under 35 U.S.C. 119 to Chinese Patent Application No. 201510051623.6 (CN), filed 30 Jan. 2015.

TECHNICAL FIELDS

The present invention relates to the field of lubricant system for medical devices and methods of applying the lubricant to the surface of medical devices to reduce the penetration forces of medical devices going through tissues or to reduce cutting forces of medical devices separating tissues, thereby reducing pain caused by the medical devices being used.

BACKGROUND

For many medical devices, such as injection needles, surgical suture needles, scalpels, medical catheters and the like, their penetration, cutting and friction forces are directly related to patients' pain and/or discomfort when the medical devices are being used. In order to reduce these forces, coating lubricant on surfaces of medical devices has been very effective. Siloxanes are widely appreciated materials as coated lubricant. However, it is an ever-stop challenge to increase the binding forces of siloxanes with the surface of medical devices and simultaneously to minimize the frictional forces between the tissues and medical devices. Adopted in the prior art, the polydimethylsiloxane, such as Dow Corning DC-360, are used as lubricants to reduce frictional forces and are cross-linked to the surface of medical devices by siloxanes with amino functional groups, such as Dow Corning MDX-4159. Major drawbacks of this type of lubricants are their very long curing time. According to product literature of Dow Corning, the curing requires 7-10 days in ambient conditions. Attempts have been made to accelerate the curing process with different formulations and methods, as described in U.S. Pat. No. 5,911,711, heating was used to accelerate the cure of the first layer of coating, then low viscosity polydimethylsiloxane was coated on top of the first layer of coating to reduce friction. Even though the heating method accelerated the curing process, the production processes are still greatly restricted. Obviously the outer layer lubricant of such lubricant system is often liquid, most of which will be erased at the time of first use, if applied to the surgical suture needles and scalpels and the like which require repeated penetrating or cutting tissues, their lubricating performance is significantly reduced thereafter. Even when applied to injection needles, if liquid medicine needs to be drawn from the ampere bottles, most of the liquid lubricant will also be erased in first time penetration, then the tissue penetration forces during injection will be greatly increased. If applied to medical catheters, excess liquid siloxane at inner surface of catheters may also react with biological medications or proteins in body fluid. People also used multiple coating layers and long-time high-temperature heating method to implement a fully cured lubricating film, as described in US patent 2013/0209664a1, medical suture needles are coated with 2 to 3 layers, and each coating is often heated to around 200° C. for many hours, which inevitably increases the production cost. Obviously, medical catheters and plastic hubs of injection needles cannot be at such high temperature without deformation.

Invention

The present invention mainly solves the technical problem of providing a lubricant system and methods of use, the surfaces of medical devices are coated at least once, a solid lubrication film can be quickly formed in ambient conditions, and the film has a very excellent lubricating performance.

To solve the above technical problem, the present invention provides a medical device lubricant system comprises siloxane polymers with viscosity greater than 100 centistokes and cross-linking agents that can promote siloxane polymers curing rapidly in ambient conditions. Said ambient conditions are the clean environment necessary for medical device productions without further defining any environmental parameters. Said rapid curing can be realized within 5 minutes, and can also be realized according to different needs and applications within extended curing time.

In a preferred embodiment, said siloxane polymers comprise selected compounds defined by the following structure:

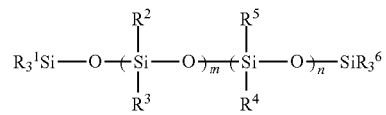

Wherein m+n is an integer between 6 to 2000; the chain length of $R(^{1/2/3/4/5/6})$ is 1~20; R group are an alkyl group, a cycloalkyl group, an aryl group and mixture thereof but not limited thereto; $R^1$, $R^2$, $R^3$, $R^4$, $R^5$, $R^6$ are the same or different.

In a preferred embodiment, said siloxane polymers' viscosity is between 100 centistokes to 30,000 centistokes at 25° C., and the weight average molecular weight of the siloxane polymers is between 6000 to 90000.

In a preferred embodiment, said siloxane polymers comprise selected hydroxy siloxane polymers defined by the following structure:

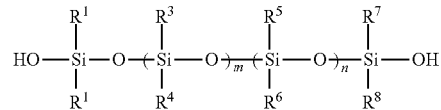

Wherein m+n is a integer between 150 to 1000; R group are an alkyl group, an aryl group, trifluoro propyl and mixture thereof but not limited thereto; $R^1$, $R^2$, $R^3$, $R^4$, $R^5$, $R^6$ are the same or different.

In a preferred embodiment, said hydroxy siloxane polymers' viscosity is between 1000 centistokes to 8000 centistokes at 25° C., and the weight average molecular weight of the siloxane polymers is between 30000 to 60000.

In a preferred embodiment, said lubricant further comprises siloxane coupling agent defined by the following structure:

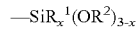

Wherein X is an integer 0≤X<2; $R^1$ are vinyl group, alkyl group terminated with amino, epoxy, halogenated groups but not limited thereto; $R^2$ are methyl, ethyl groups but not limited thereto.

In a preferred embodiment, said cross-linking agents comprise selected compounds defined by the following structure:

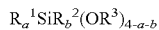
$R_a^1 SiR_b^2 (OR^3)_{4-a-b}$

Wherein a is an integer 0≤a≤2; b is an integer 0≤b<4; $R^1$ are vinyl, alkyl, vinyl groups; $R^2$ are amino group; $R^3$ are alkyl, hydrogen, alkenyl, amino, acyl, aryl, carbonyl, and imine groups.

In a preferred embodiment, further comprises catalysts, wherein said catalysts are organic tin catalysts.

In a preferred embodiment, further comprises volatile carrier solvents, wherein said volatile carrier solvents are hydrofluoroether or chlorofluorocarbon (CFC) solvents.

The present invention provides the methods of use of a medical device lubricant system comprise coating at least one layer of said lubricant on the surface of medical devices, wherein said lubricant coatings comprise any compositions described previously and reactive product thereof.

In a preferred embodiment, comprise methods of dipping, spraying, brushing, painting and jet to coat said lubricant to the surface of medical devices.

In a preferred embodiment, comprise coating of said lubricant to the metallic and polymer surfaces of medical devices.

The present invention has the beneficial effects that said lubricant system only needs to be coated on the surfaces of medical devices at least once, a solid lubrication film can be quickly formed in ambient conditions, and the film has a very excellent lubricating performance and wide applications. The methods of use are simple, easy to implement and control, and is particularly suitable for rapid automatic production lines, and thus is of great economic value.

EXAMPLES

The following are examples of the technical aspects of the present invention. Obviously, the examples are only exemplary of the technical aspects of the present invention, not in its entirety. All other embodiments, obtained by persons of skills in the field from or out of the subject invention without having to put in any creative effort, falls within the protective scope of the present invention.

Example 1

Example 1 demonstrates a comparison of the performance of a double layers of lubricant coated on the surface of injection needles according to the present invention versus a comparative product of international famous brand and of the same type.

Test method according to Chinese national standard GB/18671-2009 was used to test the performance of different lubricants coated on the surface of injection needles by measuring their penetration forces. Materials used for penetration tests are polyurethane films that have a thickness of 0.35 mm±0.05 mm and a shore (A) hardness of 85±10 to simulate human skins. Prior to testing, the polyurethane films are stored at 22° C.±2° C. for 24 hours, and tests are conducted at the same temperature.

A continuous piece of said polyurethane film is clamped to the fixing device, making sure there is no tension in the polyurethane film. The needle to be tested is fixed on the penetration device, the needle axis is perpendicular to the surface of the polyurethane film, the needle tip points to the center of the circular area of the polyurethane film to be tested, and the penetration device moves at a speed of 100 mm/minute. For each penetration, the area to be punctured on the polyurethane film is not previously used and punctured. 4 punctures are conducted for each needle in accordance with the Chinese national standard, peak penetration force for each puncture is recorded as merits to evaluate and compare the performance of different lubricants.

In the present invention, each penetration force test value is the mean value of not less than 50 needle samples tested of the same batch.

In comparative sample 1, 31G×8 mm pen needles of international famous brand are tested according to Chinese national standard GB/18671-2009, and results are placed in table 2.

Independently, a needle lubricant was prepared in accordance with the present invention as Sample 2 according to the formulation in Table 1:

TABLE 1

| Sample 2 | Weight % |
|---|---|
| 100 cst α,ω dihydroxy polydimethylsiloxane (Shandong Da-Yi Chemical Industry Co., Ltd. OH501-100) | 100 |
| 12500 cst polydimethylsiloxane (Dow Corning DC-360) | 47.50 |
| 1000 cst α,ω dihydroxy polydimethylsiloxane (Shandong Da-Yi Chemical Industry Co., Ltd. OH501-100) | 47.50 |
| cross-linking agent (Aladdin T110596/Hangzhou Guibao Chemical Co., Ltd.) | 3.28 |
| coupling agent (Aladdin A107148) | 1.48 |
| catalyst (Alfa B23612) | 0.24 |

Except for 100 cst α,ω dihydroxy polydimethylsiloxane, all other substances are mixed uniformly in no moisture condition according to a certain sequence after they are treated such as dewatering, then they are dissolved in CFC type of volatile solvent and uniformly mixed in an appropriate manner where the CFC type of volatile solvents accounts for the total mass of 92%, as Component A, 100 cst α,ω dihydroxy polydimethylsiloxane is dissolved in CFC type of volatile solvent and uniformly mixed in an appropriate manner after it is treated such as dewatering where the 100 cst α,ω dihydroxy polydimethylsiloxane accounts for the total weight of 3%, as Component B.

The cross-linking agent in table 1 is a mixture of ethyl silicate with ketoxime siloxanes, their molar ratio is 1:1.

31G pen needles are coated with lubricants as described above. Component A is applied first, after 15 seconds in ambient temperature, Component B is applied.

Penetration forces of sample 2 are tested according to Chinese national standard GB/18671-2009, and results are also placed in table 2.

TABLE 2

| | Sample 1 (Comparative Sample) | | Sample 2 | |
|---|---|---|---|---|
| Times of Penetration | Mean Penetration Forces(g) | Normalization | Mean Penetration Forces(g) | Normalization |
| 1 | 37.75 | 1.00 | 31.63 | 0.84 |
| 2 | 38.78 | 1.00 | 32.65 | 0.84 |
| 3 | 38.78 | 1.00 | 33.67 | 0.87 |
| 4 | 39.80 | 1.00 | 36.73 | 0.92 |

From the results of table 2 it can be seen that all penetration forces of sample 2 are less than those of comparative sample 1. For first and second times puncture, the penetration forces of the sample 2 after normalization are only equivalent to 84% of those of comparative sample 1, even with 4-times puncture the lubricant performance of sample 2 is better than that of the comparative sample 1, the penetration force of sample 2 is equivalent to 92% of that of comparative sample 1.

Example 2

Example 2 demonstrates a comparison of the performance of a single layer of organic siloxane compounds coated on the surface of needles according to the present invention versus comparative sample 1.

Independently, a needle lubricant was prepared in accordance with the present invention as Sample 3 according to the formulation in table 3:

TABLE 3

| Sample 3 | weight % |
|---|---|
| 12500 cst polydimethylsiloxane (Dow Corning DC-360) | 48.00 |
| 1000 cst α,ω dihydroxy polydimethylsiloxane (Shandong Da-Yi Chemical Industry Co., Ltd. OH501-100) | 48.00 |
| cross-linking agent (Aladdin T110596/Hangzhou Guibao Chemical Co., Ltd.) | 2.32 |
| coupling agent (Aladdin A107148) | 1.48 |
| catalyst (Alfa B23612) | 0.20 |

Substances in table 3 are mixed uniformly in no moisture condition according to a certain sequence after they are treated such as dewatering, then they are dissolved in CFC type of volatile solvent and uniformly mixed in an appropriate manner where the CFC type of volatile solvents accounts for the total mass of 92%.

The cross-linking agent in Table 3 is a mixture of ethyl silicate with ketoxime siloxanes, their molar ratio is 3:1.

In the same manner as in example 1, penetration forces of sample 3 are tested and results are placed in table 4.

TABLE 4

| | Sample 1 (Comparative Sample) | | Sample 3 | |
|---|---|---|---|---|
| Times of Penetration | Mean Penetration Forces(g) | Normal-ization | Mean Penetration Forces(g) | Normal-ization |
| 1 | 37.75 | 1.00 | 30.61 | 0.81 |
| 2 | 38.78 | 1.00 | 32.65 | 0.84 |
| 3 | 38.78 | 1.00 | 33.67 | 0.87 |
| 4 | 39.80 | 1.00 | 34.69 | 0.87 |

From the results of table 4 it can be seen that all penetration forces of sample 3 are less than those of comparative sample 1. The penetration forces of the sample 3 after normalization are only equivalent to 81% of those of comparative sample 1, reduced 19%, even with 4-times puncture the lubricant performance of sample 3 is better than that of the comparative sample 1, the penetration force of sample 3 is equivalent to 87% of that of comparative sample 1, reduced 13%.

Example 3

Example 3 demonstrates a comparison of the performance of coating the coupling agent alone first as a primer to the surface of needles, then coating the rest of compounds after the solvent is volatilized according to the present invention versus comparative sample 1.

Independently, a needle lubricant was prepared in accordance with the present invention as Sample 4 according to the formulation in table 5:

TABLE 5

| Sample 4 | Weight % |
|---|---|
| coupling agent (Aladdin A107148) | 100 |
| 12500 cst polydimethylsiloxane (Dow Corning DC-360) | 48.72 |
| 1000 cst α,ω dihydroxy polydimethylsiloxane (Shandong Da-Yi Chemical Industry Co., Ltd. OH501-100) | 48.72 |
| cross-linking agent (Aladdin T110596/Hangzhou Guibao Chemical Co., Ltd.) | 2.35 |
| catalyst (Alfa B23612) | 0.21 |

The coupling agent in table 5 is dissolved in CFC type of volatile solvent after it is treated where coupling agent accounts for the total weight of 3%, as Component C.

All other substances in table 5 are mixed uniformly in no moisture condition according to a certain sequence, then they are dissolved in CFC type of volatile solvent and uniformly mixed in an appropriate manner where the CFC type of volatile solvents accounts for the total mass of 92%, as Component D.

The cross-linking agent in Table 5 is a mixture of ethyl silicate with ketoxime siloxanes, their molar ratio is 3:1.

31G pen needles are coated with lubricants as described above. Component C is applied first, after 15 seconds in ambient temperature, Component D is applied.

In the same manner as in example 1, penetration forces of sample 4 are tested and results are placed in table 6.

TABLE 6

| | Sample 1 (Comparative Sample) | | Sample 4 | |
|---|---|---|---|---|
| Times of Penetration | Mean Penetration Forces(g) | Normal-ization | Mean Penetration Forces(g) | Normal-ization |
| 1 | 37.75 | 1.00 | 34.69 | 0.92 |
| 2 | 38.78 | 1.00 | 35.71 | 0.92 |
| 3 | 38.78 | 1.00 | 36.73 | 0.96 |
| 4 | 39.80 | 1.00 | 37.75 | 0.95 |

From the results of table 6 it can be seen that all penetration forces of sample 4 are less than those of comparative sample 1. The penetration forces of the sample 4 after normalization are only equivalent to 92% of those of comparative sample 1, and with 4-times puncture the penetration force of sample 4 is equivalent to 95% of that of comparative sample 1.

Example 4

Example 4 demonstrates a comparison of the performance of lubricant coated on the surface of non-patient end (NP) needles of pen needles according to the present invention penetrating the rubber septum of injection pen refills versus a comparative product of international famous brand and of the same type (sample 6).

Independently, a needle lubricant was prepared in accordance with the present invention as Sample 5 according to the formulation in table 7:

TABLE 7

| Sample 5 | weight % |
| --- | --- |
| 100 cst polydimethylsiloxane (Dow Corning DC-360) | 50.00 |
| 12500 cst polydimethylsiloxane (Dow Corning DC-360) | 18.00 |
| 1000 cst α,ω dihydroxy polydimethylsiloxane (Shandong Da-Yi Chemical Industry Co., Ltd. OH501-100) | 25.00 |
| cross-linking agent (Aladdin T110596/Hangzhou Guibao Chemical Co., Ltd.) | 3.50 |
| coupling agent (Aladdin A107148) | 3.10 |
| catalyst (Alfa B23612) | 0.40 |

Substances in table 7 are mixed uniformly in no moisture condition according to a certain sequence, then they are dissolved in CFC type of volatile solvent and uniformly mixed in an appropriate manner where the CFC type of volatile solvents accounts for the total mass of 97%.

The cross-linking agent in Table 7 is a mixture of ethyl silicate with ketoxime siloxanes, their molar ratio is 2:1.

Materials used for penetration tests are rubber septum of injection pen refills, needles coated with lubricant are the non-patent end needles of pen needles, all other conditions are the same as example 1. Penetration forces are measured for sample 5 and sample 6, and results are placed in table 8.

TABLE 8

| Times of Penetration | Sample 6 (Comparative Sample) | | Sample 5 | |
| --- | --- | --- | --- | --- |
| | Mean Penetration Forces(g) | Normalization | Mean Penetration Forces(g) | Normalization |
| 1 | 109.18 | 1.00 | 85.71 | 0.79 |
| 2 | 119.39 | 1.00 | 103.06 | 0.86 |
| 3 | 126.53 | 1.00 | 114.28 | 0.90 |
| 4 | 138.77 | 1.00 | 123.47 | 0.89 |

From the results of table 8 it can be seen that all penetration forces of sample 5 are less than those of comparative sample 6. The penetration forces of the sample 5 after normalization are only equivalent to 79% of those of comparative sample 6, reduced 21%, even with 4-times puncture the lubricant performance of sample 5 is better than that of the comparative sample 6, the penetration force of sample 6 is equivalent to 89% of that of comparative sample 6, reduced 11%.

If one of the cross-linking agents in above examples, ketoxime siloxanes, directly contact with human skin, they can cause allergic skin reactions. However when they are used as cross-linking agents, hydrolysis crosslinking reactions will occur to the ketoxime siloxanes in ambient condition, releasing all the ketoxime substance and forming solid three-dimensional structure of organic siloxane films. The above mentioned ketoxime substances at ambient temperature are extremely volatile, leaving only the non-toxic organic siloxanes. In the above examples, each needle theoretically releases 0-3 μg of ketoximino substance, the residual amount is not detected after volatilizing in ambient condition.

Although the present invention a medical device lubricant system and methods of use are only applied to the lubrication of pen needles as examples, when they are applied to medical grade metallic and non-metallic surfaces of medical devices, such as injection and infusion needles, surgical suture needles, scalpels, medical catheters, and the like, their excellent lubrication performance is also significantly.

Although illustrative embodiments of the present invention have been described herein with reference to the examples, it is not intend to restrict the protective scope of the invention. Any equivalent structural or procedural change made from or out of the description of this invention or direct or indirect use thereof in any related technical field fall within the protective scope of this patent.

The invention claimed is:

1. A medical device lubricant system, comprising
an organic lubricant film having a three-dimensional structure formed on a medical device within five minutes of crosslinking cross-linkable siloxane polymers in the presence of a crosslinking agent at ambient temperature;

wherein:
the three-dimensional structure comprises a solid structure having a portion of the cross-linkable siloxane polymers stored uncrosslinked and liquid within the solid structure during the crosslinking; and
the lubricant film is configured to release the liquid siloxane polymers as a liquid lubricant when pressure is applied thereto,
wherein the siloxane polymers comprise a polymer having the following formula:

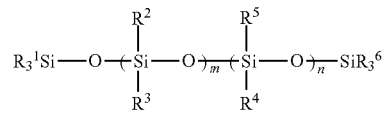

wherein:
$R^1$, $R^2$, $R^3$, $R^4$, $R^5$, and $R^6$ each independently represent an alkyl group, an aryl group, or a combination thereof,
$R^1$, $R^2$, $R^3$, $R^4$, $R^5$, and $R^6$ each independently have a chain length in a range of from 1 to 20, and
a sum of m+n is an integer in a range of from 6 to 2,000.

2. The medical device lubricant system according to claim 1,
wherein the crosslinking agent comprises a compound having the following formula:

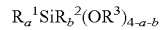

wherein:
$R^1$ represents a vinyl or alkyl group,
$R^2$ represents an amino group,
$R^3$ represents an alkyl, hydrogen, alkenyl, amino, acyl, aryl, carbonyl, or imine group,
$0 \leq a \leq 2$ is satisfied, and
$0 \leq b < 4$ is satisfied.

3. The medical device lubricant system according to claim 2, wherein the lubricant film further comprises a siloxane coupling agent having the following formula:

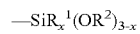

where:
$R^1$ represents a vinyl group or an alkyl group terminated with an amino, epoxy, or halogenated group;
$R^2$ represents a methyl or ethyl group; and $0 \leq x < 2$ is satisfied.

4. The medical device lubricant system according to claim 2, wherein $R^3$ represents a ketoxime group as the imine group.

5. The medical device lubricant system according to claim 1, wherein a viscosity of the siloxane polymers is in a range of from 100 to 30,000 centistokes at a temperature of 25° C., and a weight average molecular weight of the siloxane polymers is in a range of from 6,000 to 90,000.

6. The medical device lubricant system according to claim 1, wherein
the lubricant film further comprises a siloxane coupling agent having the following formula:

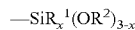

where:
R$^1$ represents a vinyl group or an alkyl group terminated with an amino, epoxy, or halogenated group;
R$^2$ represents a methyl or ethyl group; and $0 \leq x < 2$ is satisfied.

7. The medical device lubricant system according to claim 1, wherein the lubricant film is formed in the presence of an organic tin catalyst.

8. The medical device lubricant system according to claim 1, wherein the lubricant film further comprises a volatile carrier solvent selected from the group consisting of a hydrofluoroether solvent and a chlorofluorocarbon solvent.

9. The medical device lubricant system according to claim 1, wherein:
the solid structure of the lubricant film is microscopically porous; and
the lubricant film is configured to partially and continuously release the liquid siloxane polymers under pressure caused by penetration or friction, which improves lubrication of the surface of the medical device, resulting in reduced frictional force and prolonged service life of the lubricant film, and avoidance of a situation in which there is no lubricant on a frictional surface of the medical device due to the lubricant being smeared away as the frictional surface slides.

10. The medical device lubricant system according to claim 1,
wherein:
the siloxane polymers have a viscosity in a range of from 100 centistokes to 30,000 centistokes at a temperature of 25° C.

11. A method for producing the medical device lubricant system according to claim 1, comprising:
forming at least one layer of the lubricant film on a surface of the medical device by coating a composition comprising the siloxane polymers and the crosslinking agent on the surface of the medical device.

12. The method according to claim 11, wherein the composition is coated on the surface of the medical device by spraying, brushing, painting, or jet coating the composition on the surface, or dipping the surface of the medical device in the composition.

13. The method according to claim 11, wherein the lubricant film is formed on a metallic and/or polymer surface of the medical device.

14. A medical device lubricant system, comprising
an organic lubricant film having a three-dimensional structure formed on a medical device within five minutes of crosslinking cross-linkable siloxane polymers in the presence of a crosslinking agent at ambient temperature;
wherein:
the three-dimensional structure comprises a solid structure having a portion of the cross-linkable siloxane polymers stored uncrosslinked and liquid within the solid structure during the crosslinking; and
the lubricant film is configured to release the liquid siloxane polymers as a liquid lubricant when pressure is applied thereto,
wherein the siloxane polymers comprise hydroxy siloxane polymers having the following formula:

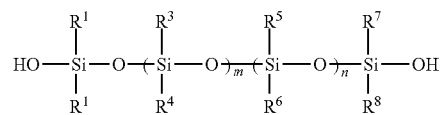

where:
R$^1$, R$^2$, R$^3$, R$^4$, R$^5$, R$^6$, R$^7$ and R$^8$ each independently represent an alkyl group, an aryl group, trifluoro propyl, or a combination thereof, and
a sum of m+n is an integer in a range of from 150 to 1,000.

15. The medical device lubricant system according to claim 14,
wherein the crosslinking agent comprises a compound having the following formula:

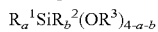

wherein:
R$^1$ represents a vinyl or alkyl group,
R$^2$ represents an amino group,
R$^3$ represents an alkyl, hydrogen, alkenyl, amino, acyl, aryl, carbonyl, or imine group,
$0 \leq a \leq 2$ is satisfied, and
$0 \leq b < 4$ is satisfied.

16. The medical device lubricant system according to claim 14, wherein a viscosity of the hydroxy siloxane polymers is in a range of from 1,000 to 8,000 centistokes at a temperature of 25° C., and a weight average molecular weight of the hydroxy siloxane polymers is in a range of from 30,000 to 60,000.

* * * * *